United States Patent [19]

Coleman et al.

[11] Patent Number: 4,622,974

[45] Date of Patent: Nov. 18, 1986

[54] APPARATUS AND METHOD FOR IN-VIVO MEASUREMENTS OF CHEMICAL CONCENTRATIONS

[75] Inventors: Jerry T. Coleman; Michael J. Sepaniak, both of Knoxville, Tenn.

[73] Assignee: University of Tennessee Research Corporation, Knoxville, Tenn.

[21] Appl. No.: 587,234

[22] Filed: Mar. 7, 1984

[51] Int. Cl.$^4$ .............................................. A61B 5/00
[52] U.S. Cl. .................................... 128/634; 356/440
[58] Field of Search ............... 128/633, 634, 665, 666; 356/432, 436, 440

[56] References Cited

U.S. PATENT DOCUMENTS

| | | | |
|---|---|---|---|
| 3,068,742 | 12/1962 | Hicks et al. | 128/634 |
| 3,136,310 | 6/1964 | Meltzer | 128/634 |
| 3,273,447 | 9/1966 | Frank | 128/675 X |
| 3,814,081 | 6/1974 | Mori | 128/634 |
| 4,003,707 | 1/1977 | Lübbens et al. | 128/634 X |
| 4,200,110 | 4/1980 | Peterson et al. | 128/634 |
| 4,201,222 | 5/1980 | Haase | 128/634 |
| 4,344,438 | 8/1982 | Schultz | 128/634 |
| 4,449,535 | 5/1984 | Renault | 128/634 |
| 4,476,870 | 10/1984 | Peterson et al. | 128/634 |
| 4,548,505 | 10/1985 | Ono | 128/634 X |

OTHER PUBLICATIONS

Goldstein et al., European patent application Ser. No. 73558, published Mar. 9, 1983.

*Primary Examiner*—William E. Kamm
*Assistant Examiner*—John C. Hanley
*Attorney, Agent, or Firm*—Luedeka & Neely

[57] ABSTRACT

A method and apparatus in which a blunt interior needle is positioned within a larger external needle and a sample cavity is formed at the blunt end of the interior needle. An optical fiber extends from the sample cavity up the interior needle and to a light source and light detector. A reflective surface is placed at the end of the sample cavity reflects light back to the optical fiber. A beam splitter separates the incident and reflected light.

To make an in-vivo measurement of chemical concentrations in a body, the needle is inserted into the body and fluids are aspirated into the sample cavity. Light is then transmitted to the cavity by the optical fiber and is transmitted from the cavity to a detector by the same fiber. By measuring the amount of light reflected, one can determine the amount of light absorbed in the cavity and may thus determine concentrations of selected chemicals.

1 Claim, 9 Drawing Figures

APPARATUS AND METHOD FOR IN-VIVO MEASUREMENTS OF CHEMICAL CONCENTRATIONS

The present invention relates to instruments for determining chemical concentrations by measuring light absorption at one or more selected frequencies, and particularly relates to an apparatus and method for making in-vivo measurement of chemical concentrations in a body fluid by measuring the light absorption characteristics of the body fluid.

Laboratories have long used spectrophotometric measurements, including absorbance measurements, as a method of analysis for body fluids in the diagnosis and treatment of illness. Albumin, alcohol, calcium, total bilirubin, cholestrol, chloride, glucose, lactic acid. Magnesium and phosphorous are routinely assayed in the laboratory using spectrophotometry. A bichromatic method is usually employed for the absorption measurements in order to correct for interfering species.

Typically, spectrophotometric analysis are done in automated machines that have increased the efficiency of the clinical laboratory, but there are still several time consuming steps common to all such tests. Basically, the patient must be moved to a special laboratory or procedure room for the removal of a sample from his body, and the sample is generally picked up and delivered to the clinical laboratory. The time delay in the delivery of the sample to the clinical laboratory and any delays in the laboratory may allow degregation of the sample so that the accuracy of the analysis is compromised. To avoid the numerous problems associated with the laboratory analysis of body fluids and to provide faster results, the present invention provides an instrument for making in-vivo measurements of chemical concentrations in body fluids.

A single optical fiber is used in the present invention to transmit light from an exterior surface into the body to spectroscopically determine chemical concentrations in body fluids. Fiber optic bundles have been used for various clinical measurements and for the in-vivo observation of body organs. However, these devices are generally too bulky to permit site-specific, non-traumatic measurements in all body fluids, including the interstitial fluids of soft tissue.

In accordance with the present invention, an apparatus for making in-vivo determinations of the concentrations of light absorbing chemicals in the body fluids of a body includes a needle with a needle point for penetrating the body to a region of biological fluids to be tested. A reflective surface is disposed within the needle and adjacent to the needle point in an orientation generally perpendicular to the needle, and a sample cavity is disposed within the needle for receiving and containing samples of biological fluid. The reflective surface is positioned between the needle point and at least a portion of the sample cavity.

An ingress pathway is provided from the biological fluids outside of the needle to the sample cavity, and biological fluids are selectively admitted through the ingress into the sample cavity. An optical fiber is disposed within the needle and has first and second ends. The first end of the optical fiber is disposed at the sample cavity in an opposed relationship with the reflective surface in the sample cavity so that light may be transmitted into the sample cavity and reflected back through the sample cavity to the first end of the optical fiber. The distance between the reflective surface and the first end of the optical fiber is defined as one-half the distance of the sample cavity light path.

A light system transmits light into the second end of the optical fiber and a detection system detects the intensity of the light eminating from the second end of the optical fiber simultaneously with the transmission of light into the second end of the optical fiber. Thus, the concentration of a light absorbing chemical in the biological fluid within the sample cavity may be determined by measuring the light guided into the sample cavity through the optical fiber, transmitted through the sample cavity twice, and transmitted by the same fiber to the detector.

Preferably, the apparatus includes a second needle with a blunt end. The second needle is disposed within the other needle and the blunt end is disposed adjacent the needle point. The optical fiber is disposed within the second needle and its first end is positioned at a distance of one-half of the sample cavity light path distance from the blunt end of the needle. The reflective surface is mounted on the blunt end of the needle, and the sample cavity is defined by the reflective surface, the second needle walls, and the first end of the optical fiber. An aspirating port is connected to the second needle for selectively aspirating the second needle to draw biological fluids from outside of the first needle into the sample cavity through the ingress.

In the preferred embodiment, the ingress is at least one aperture in the wall of the second needle between the reflective surface and the first end of the optical fiber. In another embodiment, the reflective surface and the ingress means are provided by a reflective mesh that is mounted on the blunt end of the second needle. The reflective mesh will reflect at least a portion of the light transmitted from the first end of the optical fiber and will allow ingress of biological fluids into the sample cavity when a negative pressure is created within the sample cavity by aspirating through the aspiration port.

In accordance with another embodiment of the present invention, two sources of light having two different wavelengths are used. An optical system is provided for transmitting the two different wavelengths of light to and into the second end of the optical fiber at different times, and a detection system measures the intensity of the light of the light at the two different wavelengths that is transmitted through the fiber and sample cavity. In this construction the measured intensity at the two different wavelengths can be used to simultaneously determine the concentration of two chemicals in the body fluid, provided the molar absortivities of the chemicals at the two wavelengths are known.

The instrumentation of the present invention provides a convenient in-vivo analysis of body fluids and provides true absorbance values of body fluids. Currently, the instrumentation used for remote absorbance measurements is totally unsuitable for in-vivo measurements and the equipment that is used for in-vivo measurements produces relative values, that is, no true analytical values, such as light absorbance. In the preferred embodiment of the invention, the sample cavity is contained inside a hypodermic needle which makes it suitable for subcoutaneous insertion and autoclaving. The probe is small and requires an extremely small volume of fluid to fill the sample cavity, and after analysis, the fluid may be expelled from the probe back into the patient. With the wide use of lasers in the hospital today, existing layer equipment can be adapted for use in this invention and would, thus, reduce the expense of the overall system.

The present invention may best be understood by reference to the following Detailed Description of preferred embodiments when considered in conjunction with the Drawings in which.

Figure 1:
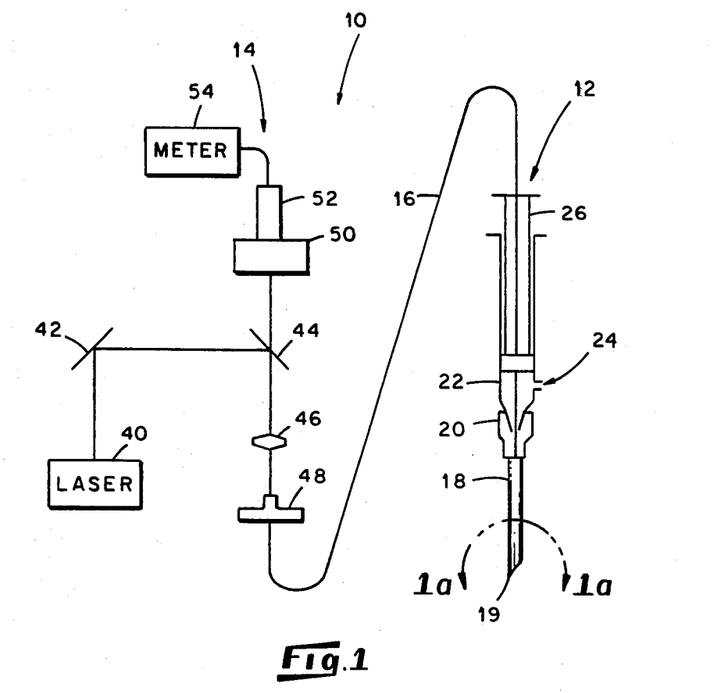
FIG. 1 is a somewhat diagrammatical view of the in-vivo apparatus for determining chemical concentrations in a body fluid.

Referring now to the drawings in which like reference characters designate like or corresponding parts throughout the several views, there is shown in FIG. 1 a measuring apparatus 10 for making in-vivo determinations of the concentrations of light absorbing chemical in biological fluids of a body. Basically, the apparatus 10 includes two parts, a probe 12 and an optics system 14, and the two parts are interconnected by an optical fiber 16.

The probe 12 includes an exterior needle 18 that is preferably a fifteen gauge by two inch hypodermic needle. The base of needle 18 is attached to needle mount 20 that is in turn affixed to a tuberculin syringe 22. At a position on the lower end of the syringe 22, an aspiration port 24 is formed in the syringe for providing aspiration as will be hereinafter described in greater detail. The syringe 22 also includes a plunger 26, and the optical fiber 16 is fixedly mounted through the center of the plunger 26 and is positioned in an interior needle that is within the needle 18. In this construction, the position of the optical fiber 16 within the needle 18 may be adjusted by moving the plunger 26 within the barrell of the syringe 22.

Figure 1A:
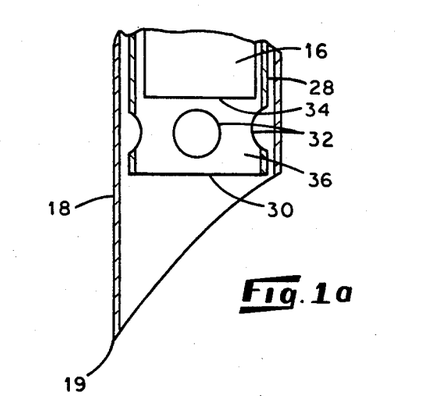
FIG. 1a is a detailed cross-sectional view of the end of the interior and exterior needles and fiber optic of FIG. 1.

FIG. 1 includes a detailed cross-sectional view, FIG. 1A, of the lower end of the exterior needle 18. As shown in FIG. 1A, the exterior needle 18 has a sharp needle point 19, and a blunt interior needle 28 is mounted within the exterior needle 18. Preferably, the interior needle 28 is a nineteen gauge by one and one-half inch hypodermic needle that were specially made by Becton-Dickison, N.J., to have a smooth reflective inner wall that is more reflective than conventional disposable hypodermic needle. The specially made interior needles 28 were prepared by drawing stainless steel tubing through dies, first with, then without, an internal mandrel in decreasing gauges to the final gauge size. The tubing is then straightened out and fabricated into needles. The increased reflectivity of the interior needle 28 is needed in order to provide a greater transmittance of light through a sample cavity as will be described hereinafter.

The interior needle 28 is silver soldered and sealed within the exterior needle 18 so that the aspiration port 24 is in fluid communication with the interior needle, but not with the exterior needle directly. Thus, aspiration using the aspiration port 24 is accomplished through the interior needle 28. A blunt end is formed on the interior needle 28 and a reflective surface 30 is mounted completely covering and sealing the blunt end of the needle. In the embodiment shown, the reflective surface is constructed a aluminum foil and is attached to the needle 28 using optically transparent epoxy adhesive.

An optical fiber 16 is positioned in a spaced-apart substantially coaxial relationship with the interior needle 28. In the preferred embodiment, the optical fiber 16 has a diameter of 600 micrometers, and, thus, the size of the optical fiber is such that it will not interfere with aspiration through the interior needle 28. The lower end 34 of the optical fiber 16 is positioned at a selected distance from the reflective surface 30, within the range of 0.25 mm to 2.5 mm, and preferably a distance of 0.9 mm. The distance between the end 34 of the optical fiber 16 and the reflective surface 30 is one-half the sample cavity light path distance.

Four apertures 32 are drilled in the interior needle 28 having a diameter of 0.015 inches and being positioned approximately 0.045 inches from the reflective surface 30. The holes 32 provide an ingress and egress pathway from the exterior of the needle 18 to the interior of the needle 28. The volume of defined between the end 34 of the optical fiber 16, the reflective surface 30 and the interior walls of the interior needle 28 is the sample cavity 36. The distance between the optical fiber end 34 and the reflective surface 30 will be defined as one-half the sample cavity light path distance, although it is recognized that the average light path distance is somewhat greater since the light will be transmitted and reflected at angles and will be reflected from the interior walls of the interior needle 28.

The probe 12 is connected to an optics system 14 which includes a laser 40, for example an argon ion laser producing radiation of 0.025 watts at 4579 angstroms manufactured by Spectra-Physics, Model 171. A laser beam is transmitted to a beam splitter 44 which transmits fifty percent of the light and reflects fifty percent of the laser beam toward a 35 mm focal length quartz lens 46 which focuses the laser beam onto the end of the optical fiber 16 which is mounted and positioned by a fiber postioner 48. Light is also transmitted out of the optical fiber 16 in the fiber positioner 48 and is transmitted through the lens 46 to the beam splitter 44. Fifty percent of this light is reflected and fifty percent of the light is transmitted to the monochromator and optical filter system 50. The system 50 includes an entrance slit and an iris which spacially reject reflected radiation from the surface of the lens and the input end of the optical fiber and, thus, minimize the detection of stray radiation. Neutral density filters are placed within the monochromator and optical filter system 50 to obtain the desired magnitude of light which is then fed into a photomultiplier tube, for example, the photomultiplier tube manufactured by RCA, Model No. IP28-A. The voltage from the photomultiplier tube 52 is supplied to a meter 54 which provides output information.

In operation, the probe 12 is inserted into a body so that the needle point 19 is positioned in the region of biological fluids to be tested. A suction is then placed on the aspiration port 24 and the biological fluids are drawn into the sample cavity 36. A laser beam having a power level of about 20 milliwatts is transmitted from the laser 40, reflected by the reflective surface 42 and the beam splitter 44, focused by the lens 46 and transmitted by the optical fiber 16 to the optical fiber end 34. The light then travels through the fluid in the sample cavity 36, against the reflective surface 30 and back through the biological fluid to the optical fiber 16 and back to the fiber positioner 48. The light that was reflected back into the optical fiber end 34 was a combination of reflected light from the reflective surface 30, the inner walls of the needle 28 and the reflection of the body fluid itself within the cavity 36. Once the light that is reflected back to the fiber positioner 48, it passes through the lens 46 and fifty percent of it is passed through the beam splitter 44 and into the monochromator and optical filter system 50. The photomultiplier 52 then creates a signal that corresponds to the magnitude of the light intensity that it receives which is indicated on the meter 54. Thus, the reading of the meter 54 will correspond to the light that is received by the photomultiplier tube 52 which corresponds to the amount of light that was reflected through the optical fiber 16 after it passed through the sample cavity 36.

The apparatus 10 may be calibrated using a transparent substance in the sample cavity 36 so that when biological fluid is placed in the cavity 36, the reading on the meter 54 will correspond to the light absorbed by the biological fluid. That is, the logarithim of the ratio of the reading of the meter 54 when nothing is present in the sample cavity and a reading when body fluid is contained in the sample cavity will correspond to the absorbance by the chemical contained in the body fluid within the sample cavity.

Figure 2A:
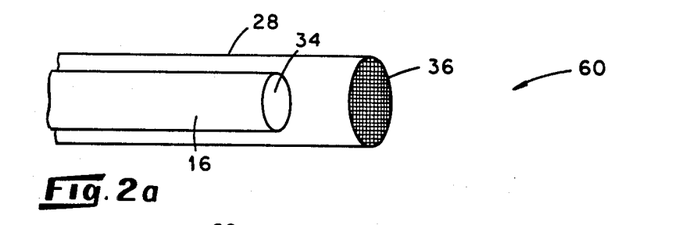
FIGS. 2a; 2b and 2c show three alternate embodiments of the interior needle of the present invention which defines a sample cavity for receiving biological fluids.
Figure 2B:
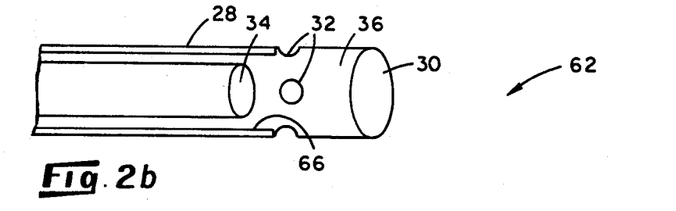
Figure 2C:
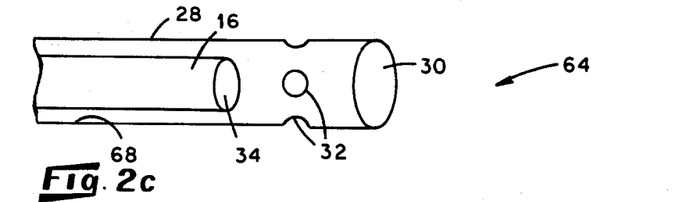

Referring now to FIGS. 2a, 2b, and 2c there is shown three different embodiments, 60, 62 and 64, of the interior needle 28. In the embodiment 60, a gold foil 36 is mounted on the blunt end of the needle 28 to function as the reflective surface and as a means for allowing ingress and egress of body fluids between the needle 28 and the body of the subject. The gold mesh 36 may be chosen to provide a desired reflectivity and the mesh will also act as a filter of the body fluids entering the needle 28. Thus, the mesh size may also be chosen to provide a desired filtering action.

The second embodiment 62 shown in FIG. 2b retains the use of a solid reflective surface 30 and apertures 32, and a reflective coating 66 is applied to the interior walls of the needle 28 to improve the transmission of light through the needle 28. The reflective coating 66 extends at least partially into the sample cavity area 36 and would, thus, improve the light transmission within the cavity. It is understood that the reflective coating 66 is shown in an exaggerated size for purposes of clarity of illustration. The composition of the reflective coating is not critical, but is preferably a metal, such as aluminum, deposited on the interior of the needle 28, or an inserted sleeve.

The embodiment 64 shown in FIG. 2c also includes a solid reflective surface and holes 32, but further includes a blackened interior coating 68 on the needle 28. The coating 68 will absorb radiation that strikes the interior of the needle 28 and, thus, the light path between the optical fiber end 34 and the reflective surface 30 includes only direct light paths and would not include light paths where light impinged on the interior walls of the needle 28.

A critical dimension of the probe 12 is the distance between the optical fiber end 34 and the reflective surface 30 because this distance defines the sample cavity light path length. As the distance between the reflective surface 30 and the optical end 34 increases, the sensitivity of the apparatus will increase, but the limit of detection decreases. Thus, for most biological fluids, there is an optimum position for the optical fiber end 34 and there is a range of positions within which the probe 12 will work well.

Figure 3:
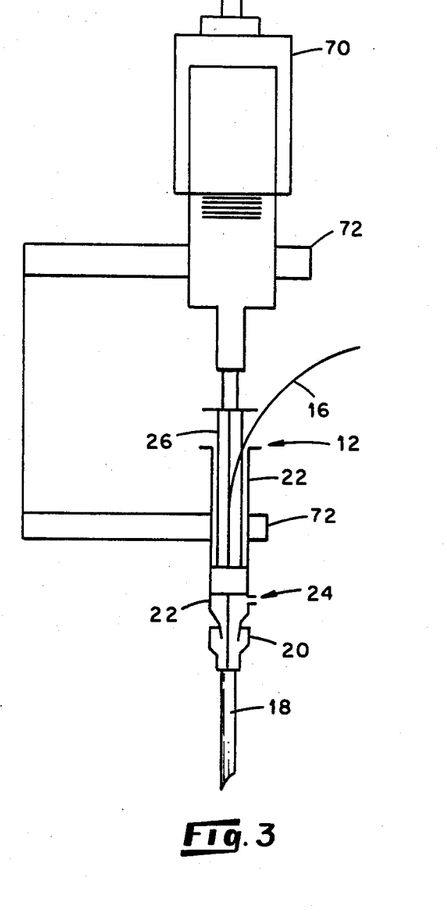
FIG. 3 is a somewhat schematic diagram of the probe of the present invention utilizing a micrometer to adjust the position of an optical fiber.

This optimum position and range is discussed with regard to FIG. 3 in which there is shown yet another embodiment of the invention. Both a micrometer 70 and the probe 12 are mounted in a bracket 72 with the micrometer 70 connected to move the plunger 26 of the probe. Since the plunger 26 is fixedly connected to the optical fiber 16, the micrometer 70 may be used to move the fiber 16 axially within the needle 18 and, thus, is operable to move the optical fiber end 34 relative to the reflective surface 30. Once the micrometer is calibrated, the readings of the micrometer 70 will correspond to the distance between the optical fiber end 34 and the reflective surface 30, and a desired distance may be obtained by simply rotating the micrometer and observing the micrometer readings which correspond to sample cavity light path distances.

Figure 4:
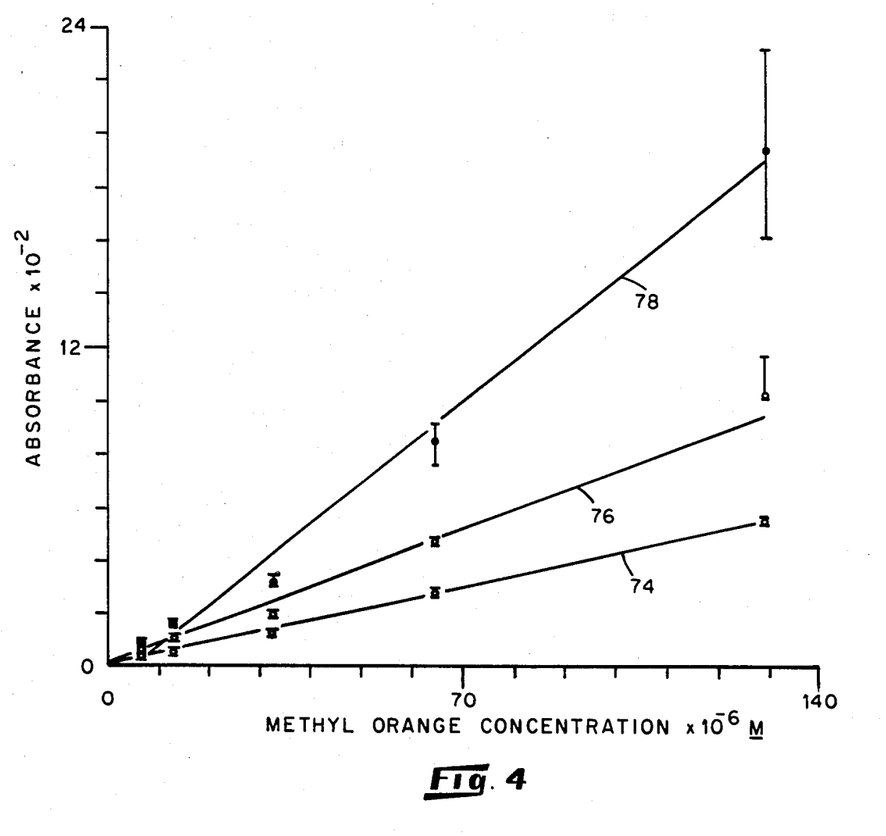
FIG. 4 is a graph showing light absorbance versus methal orange concentration in a sample cavity for three different sample cavity light path distances.
Figure 5:
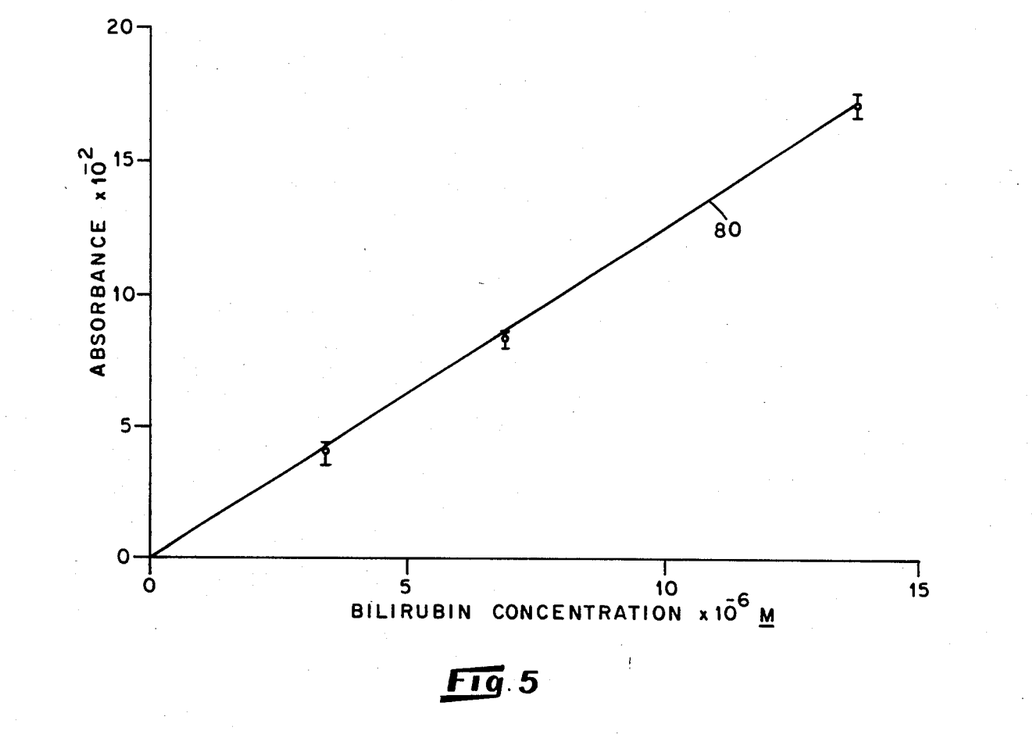
FIG. 5 is a graph showing light absorbance versus bilirubin concentration in a sample cavity for a preferred sample cavity size.

To illustrate the relationship between sensitivity and limits of detection, FIG. 5 depicts three graphs of light absorbance versus methal orange concentration in the sample cavity. The graphs in FIG. 4 were determined empirically by placing methal orange in different concentrations into the absorbance probe and measuring the light absorbance for three different path lengths. Line 74 was obtained using a path length of 0.5 mm, line 76 using a path length of 1.8 mm and line 78 using a path length of 4.3 mm. It will be recalled that the light path length is twice the distance between reflective surface 30 and optical fiber end 34.

Using the apparatus 10 shown in FIG. 1, it was empirically determined that, assuming a limit of detection at a signal to noise ratio of two, the limits of detection using a path length of 4.3 mm was 0.009 absorbance units. Using a path length of 1.8 mm, the limit of detection was found to be 0.005 absorbance units. With a path length of 0.5 mm, the limit of detection was 0.011 absorbance units. Based on these and other experimental results, it was determined that for most body fluids, the optimum path length is about 1.8 mm and that the probe would operate well only within a light path length range of about 0.5 mm to about 5.0 mm. The optimum path length was chosen to obtain a balance between sensitivity and limits of detection.

To illustrate the use of apparatus 10 for measuring concentrations of biological fluids, the apparatus was used to measure bilirubin concentration. In FIG. 5, graph 80 plots bilirubin concentrations versus absorbance in the sample cavity 36 using a light path of 1.8 mm. The bilirubin concentration was first determined using apparatus 10 and the results were verified by standard laboratory techniques. The graph of absorbance versus bilirubin concentration is shown in FIG. 6 by way of an example, but it will be understood that the probe may be used to determine concentrations of most any chemical in body fluids that may be detected spectroscopically based on the chemical's light absorption.

Figure 6:
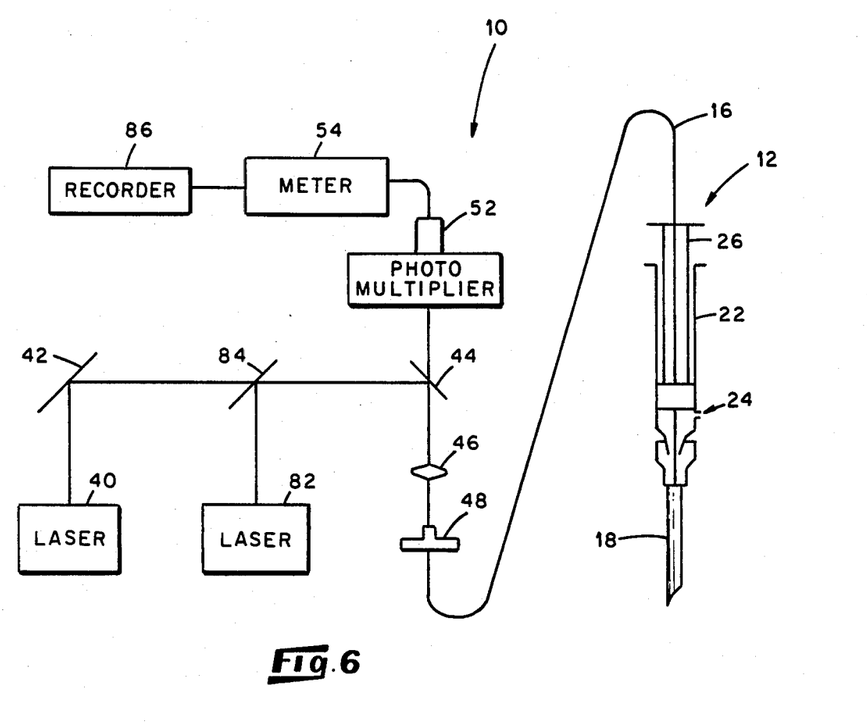
FIG. 6 is a somewhat schematic diagram of the apparatus of the present invention utilizing two lasers as light sources.

Referring now to FIG. 6, there is shown another embodiment of the apparatus 10. A second laser 82, and a dichroic filter 84 have been added along with a recorder 86. The dichroic filter 84 is chosen to transmit the beam of laser 40 and reflect the beam of laser 82. The dichroic filter 84 is interposed in the laser beam path between reflective surface 42 and beam splitter 44 so that the filter 84 transmits the light from laser 40 to the beam splitter 42. The splitter 84 is oriented so that it also receives light from the new laser 82 and reflects it along the same light path as the laser beam from laser 40. The filter 84 also reflects the light from laser 82 toward splitter 44, and both laser beams from lasers 40 and 82 are reflected by splitter 44 toward the lens 46 and into the optical fiber 16 as previously described.

The recorder 86 is a standard strip chart recorder interconnected with the meter 54. The recorder 86 simply provides a printout of the meter readings over a period of time so that subsequent calculations may be performed to determine the concentrations of various chemicals in body fluids.

In operation, laser 40 is first energized and readings are taken to determine the amount of light absorption taking place in the sample cavity at the wavelength of the laser beam produced by laser 40. Next, laser 40 is turned off and laser 82 is turned on. Then, measurements are again taken to determine the amount of light absorption taking place within the sample cavity at the wavelength of the laser 82. By using two different lasers at two different light wavelengths, information about the chemical concentration is obtained in accordance with standard spectroscopy procedures. For example, if it is known that the chemical to be tested will absorb light having a wavelength of laser 40 but it will not absorb light having a wavelength of laser 82, and an interfering chemical will absorb light of both wavelengths by the same amount then the difference in absorption obtained when using laser 40 as compared to laser 82 will correlate to the absorption of the chemical being studied. The difference between the absorption at one wavelength and the absorption at another wavelength should correspond to the absorption of the chemical being studied, and in this manner, compensation is made for the interfering chemical. It will be understood that other optical arrangements may be used to obtain different wavelengths and multiple lasers may be used to achieve greater variations in the wavelengths. Also, so long as the absorption characteristics of both the chemical to be studied and the interfering chemicals are known, corrections to compensate for the absorption of these interfering chemicals can be made using radiation of two or more wavelengths.

Referring again to FIG. 1, and particularly FIG. 1A, it will be appreciated that a reagent may be immobilized within the sample cavity 36 so that the reagent is inserted along with the probe into the region of the biological fluids to be tested. When the biological fluids are aspirated into the sample cavity 36, the reagents will react with the chemical to be tested and will change the light absorption characteristics of the chemical so that it absorbs light at a different wavelength. In this manner, if a chemical to be tested is found in the presence of an interfering chemical that absorbs light at the same wavelength, the absorption characteristics of the chemical to be tested are changed to avoid the interfering chemical. It will be understood that most any reagent may be used if it is not toxic so that an inadvertent release of any of the reagent will not harm the patient. If toxic reagents are used, a filter or semipermiable membrane should be placed over the holes 32 to permit biological fluids to enter the sample cavity but to prevent reagents from escaping the sample cavity.

As an example of reagents that may be used, in testing for bilirubin, a commonly used reagent for changing the light absorption characteristics of bilirubin is a combination of a caffine reagent, a diazio reagent and a tartrate solution. The caffine reagent is typically made of caffine, sodium benzoate, sodium acetate, and sodium. The diazoe reagent is composed of sulfanilic acid, hydrochloric acid, sodium nitrate and water. The tartrate solution is composed of sodium hydroxide and sodium tactrate. The caffine reagent can be immobilized within the sample cavity 36 to react with bilirubin when it is aspirated into the cavity.

Although particular embodiments of the invention have been discussed, it will be understood that these are examples that were described for the purposes of illustration and the invention is capable of numerous rearrangements, modifications and substitutions of parts without departing from the spirit of the invention. In particular, it is noted that the probe could be constructed of other tubular materials, such as a flexible pointed cylinder. The term needle, as it is used herein, will be understood to have a broad meaning encompassing tubular structures of varying lengths, widths and flexibility.

What is claimed is:

1. An apparatus for use in making in-vivo determinations of light absorbance of biological fluid of a body comprising:

an insertion needle with a needle point for penetrating the body to a region of the biological fluid to be tested;

a reflective surface disposed within the needle and adjacent to the needle point in an orientation generally perpendicular to the longitudinal axis of the needle;

a sample cavity disposed within said needle for receiving and containing samples of the biological fluid, said reflective surface being disposed between said needle point and at least a portion of said sample cavity;

ingress means for providing a pathway from the biological fluids from outside the needle to said sample cavity within said needle to allow ingress of fluid into said sample cavity;

a source of light;

optical fiber having a first end disposed within said needle and a second end receiving light from said light source and transmitting light to said first end, said first end of said optical fiber being disposed at said sample cavity in an opposed generally parallel relationship with said reflective surface so that light is transmitted from the first end, through said sample cavity, and reflected by said reflective surface back through said sample cavity and into said first end, the distance between said reflective surface and said first end of said optical fiber defining one-half of the length of the sample light path through the sample cavity;

means for detecting the intensity of light transmitted from said second end of said single optical fiber simultaneously with the transmission of light into said second end by said light source whereby the biological fluid is determined by transmitting light into said sample cavity through said optical fiber and measuring the intensity of light is reflected by said reflective surface that passes through said sample cavity, and reenters said first end of said optical fiber to determine the amount of light that was absorbed by the light absorbing constituents of the biological fluid in said sample cavity; and
means for adjusting the distance between said reflective surface and the first end of said optical fiber to change the length of said sample light path,
said means for adjusting the distance between said reflective surface and the first end of said optical fiber comprising a micrometer mechanically linked to said optical fiber and mechanically linked to said needle to change and indicate the position of the first end of said fiber with respect to said reflective surface.

* * * * *